United States Patent
Elg

(10) Patent No.: US 7,449,446 B2
(45) Date of Patent: *Nov. 11, 2008

(54) COMBINATION PRODUCT COMPRISING MELAGATRAN AND DEXAMETHASONE

(75) Inventor: Margareta Elg, Molndal (SE)

(73) Assignee: AstraZeneca AB, Sodertalje (SE)

( * ) Notice: Subject to any disclaimer, the term of this patent is extended or adjusted under 35 U.S.C. 154(b) by 263 days.

This patent is subject to a terminal disclaimer.

(21) Appl. No.: 10/493,625

(22) PCT Filed: Oct. 24, 2002

(86) PCT No.: PCT/SE02/01938

§ 371 (c)(1), (2), (4) Date: Apr. 23, 2004

(87) PCT Pub. No.: WO03/035079

PCT Pub. Date: May 1, 2003

(65) Prior Publication Data

US 2005/0014701 A1  Jan. 20, 2005

(30) Foreign Application Priority Data

Oct. 26, 2001  (SE) .................... 0103590

(51) Int. Cl.
*C07K 5/00* (2006.01)
*A61K 38/55* (2006.01)

(52) U.S. Cl. .................. 514/18; 514/20; 514/247; 424/9.1; 544/238; 544/239; 544/240; 560/34; 560/35; 560/168; 560/169; 562/439; 562/560

(58) Field of Classification Search .................. 514/18, 514/20, 247; 424/9.1; 544/238, 239, 240; 560/34, 35, 168, 169; 562/439, 560
See application file for complete search history.

(56) References Cited

U.S. PATENT DOCUMENTS 3,461,208 A  8/1969  Winter
6,683,054 B1 *  1/2004  Kirk .................... 514/18

FOREIGN PATENT DOCUMENTS

| WO | WO-94/29336 A1 | 12/1994 |
| WO | WO-97/23499 A1 | 7/1997 |
| WO | WO 00/64470 | 4/2000 |
| WO | WO-00/41716 A1 | 7/2000 |
| WO | WO-01/95931 A1 | 12/2001 |
| WO | WO-01/95932 A1 | 12/2001 |

OTHER PUBLICATIONS

Yi et al., Inflammation vol. 20, No. 2, 165-175 (1996).*

Bernard et al., "Efficacy and Safety of Recombinant Human Activated Protein C. For Severe Sepsis," The New England Journal of Medicine 344(10):699-709 (2001).
Saito et al., "Recombinant Hirudin for the Treatment of Disseminated Intravascular Coagulation in Patients with Haematological Malignancy," Blood Coagulation and Fibrinolysis 6:60-64 (1995).
Yamazaki et al., "Prednisolone Inhibits Endotoxin-Induced Disseminated Intravascular Coagulation and Improves Mortality in Rats: Importance of Inflammatory Cytokine Suppression," Blood Coagulation and Fibrinolysis 10:321-330 (1999).
Eisele, B., et al., "Clinical Experience with Antithrombin III Concentrates in Critially Ill Patients with Sepsis and Multiple Organ Failure," Sem. Thromb. Hemost., 24, 71-80 (1998).
Riewals, M., et al., "Treatment Options for Clinically Recognized Disseminated Intravascular Coagulation," Sem. Thromb. Hemost., 24, 53-59 (1998).
Diaz-Cremades, J.M., et al., "Use of antithrombin III in critcal patients," Intensive Care Med., 20, 577-580 (1994).
Eriksson, M., et al., "Melagatran, a Low Molecular Weight Thrombin Inhibitor, Counteracts Endotoxin-induced Haemodynamic and Renal Dysfunctions in the Pig," Thromb. Haemost., 80-1022-1026 (1998).
Erikkson, M., et al., "Effects of melagatran, an inhibitor of thrombin, on fibrin deposits, haemodynamics, and platelet count in endotoxaemic pigs," Acta Anaesthesiol. Scand., 44, 24-31 (2000).
Basu, S., et al., "Effects of melagatran, a novel direct thrombin inhibitor, during experimental septic shock," Exp. Opin. Invest. Drugs, 9(5), 1129-1137 (2000).
Martindale—The Complete Drug Reference, 32nd Edition, K. Parfitt (ed.), Pharmaceutical Press, London (1999), 1037-1039.
"Melagatran and Ximelagatran, Anticoagulant Thrombin Inhibitor," Drugs of the Future, 26(12), 1155-1170 (2001).
Margareta, E., et al., "A combination of a thrombin inhibitor and dexamethasone prevents the development of experimental disseminated intravascular coagulation in rats," Abstract—Blood, http://www.bloodjournal.org, vol. 98(11), p. 47a, (Nov. 2001).
Liu, Y.Y., "Comparison between the therapeutic effects of ginseng-aconitum-bupleurum injection and dexamethasone on septic shock complicated with disseminated intravascular coagulation induced by *E. coli* in dogs," Chung Hsi I Chieh Ho Tsa Chih Chinese Journal of Modern Developments in Traditional Medicine, 10(11), 675-6, 645 (1990), STN International, File: Medline, accession No. 91098744.
coagulation induced by E. coil in dogs, Chung Hsi I Chieh Ho Tsa Chih Chinese Journal of Modern Developments in Traditional Medicine, 10(11), 675-6, 645 (1990), STN International, File: Medline, accession no. 91098744.

* cited by examiner

*Primary Examiner*—Chih-Min Kam
(74) *Attorney, Agent, or Firm*—Morgan, Lewis & Bockius LLP

(57) ABSTRACT

There is provided a combination product comprising; (A) melagatran or a pharmaceutically acceptable derivative thereof; and (B) dexamethasone or a pharmaceutically acceptable derivative there of, wherein each of components (A) and (B) is formulated in admixture with a pharmaceutically-acceptable adjuvant, diluent or carrier, as well as the use of such a combination product in the treatment of conditions including disseminated intravascular coagulation.

14 Claims, 6 Drawing Sheets

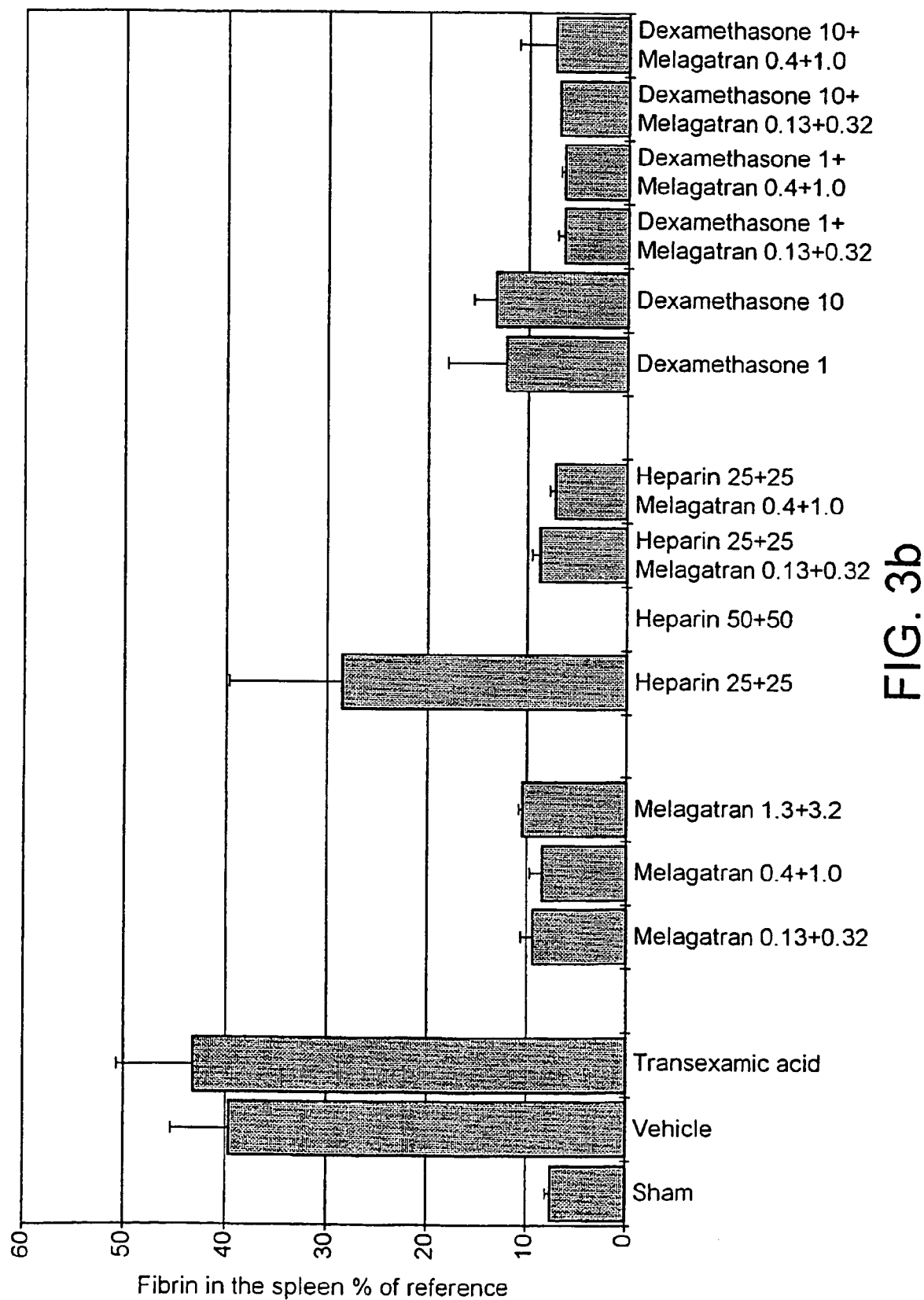

COMBINATION PRODUCT COMPRISING MELAGATRAN AND DEXAMETHASONE

RELATED APPLICATIONS

This application is a national stage filing under 35 U.S.C. 371 of International Application PCT/SE02/01938, filed Oct. 26, 2002, which claims priority from Sweden Application No. 0103590-6, filed Oct. 26, 2001, the specifications of each of which are incorporated by reference herein. International Application PCT/SE02/01938 was published under PCT Article 21(2) in English.

FIELD OF THE INVENTION

This invention relates to a new combination of pharmaceutically-active compounds.

BACKGROUND AND PRIOR ART

Blood coagulation is the key process involved in both haemostasis (i.e. the prevention of blood loss from a damaged vessel) and thrombosis (i.e. the formation of a blood clot in a blood vessel, sometimes leading to vessel obstruction).

Coagulation is the result of a complex series of enzymatic reactions.

Disseminated intravascular coagulation (DIC) is a systemic secondary thrombo-haemorrhage disorder seen in consequence of primary problems, such as infections, trauma, obstetric complications, cancer and snake bites.

The most serious clinical form of DIC is characterised by excessive consumption of coagulation proteins, deposition of fibrin and bleeding. In its least serious forms, endogenous markers of thrombin generation are produced with little or no obvious coagulation problems.

Trauma patients are at increased risk of DIC. Head trauma is a particularly common cause in children.

Sepsis may occur in about 40% of trauma patients and is an important primary cause of DIC in all patients. The clinical condition is worsened by secondary fibrinolysis, which results in the formation of, for example, fibrinogen and fibrin degradation, which interfere with normal fibrin formation and platelet function.

Fibrin deposition in DIC may lead to further organ dysfunction. DIC is a major cause of acute renal failure and it also contributes to multiple system organ failure (MOF) and death. Despite improvements in the critical care and use of broad-spectrum anti-microbial agents, the mortality rate in DIC patients with severe sepsis still is high (Eisele et al, *Sem. Thromb. Hemost.*, (1998) 24, 71).

DIC is characterised primarily by activation of procoagulants, resulting in excessive thrombin generation, hypercoagulability with intravascular fibrin formation, and platelet aggregation in the tissues, leading to thrombocytopenia (low platelet count). Further, the natural coagulation inhibitory mechanisms that neutralize thrombin fail to operate properly.

Current DIC treatments are highly individualised and are focused on treating the primary underlying disease. Without control, DIC continues despite forms of therapy directed at correcting the bleeding or thrombotic problem.

For patients with significant bleeding, to maintain haemostatic balance, replacement therapy using fresh frozen plasma (FFP), cryoprecipitate, and/or platelet concentrates is frequently used until the primary problem may be brought under control.

Endogenous anticoagulation and/or other anticoagulant treatments may be beneficial in treating DIC. Heparin has been used in patients with DIC with varying results. However, response to heparin appears to be dependent on the plasma concentration of antithrombin III (ATIII) which is usually decreased during DIC especially in patients with sepsis (Riewald and Reiss, *Sem. Thromb. Hemost.*, (1998) 24, 53). Indeed, the use of heparin in the treatment of DIC is highly controversial, and is not generally indicated in patients with the underlying problem of trauma.

Substitution with ATIII has been found to reduce mortality in endotoxin animal models, and also in critically ill patients with sepsis (Diaz-Cremades et al, *Intensive Care Med.*, (1994) 20, 577; Eisele et al, *Sem. Thromb. Hemost.*, (1998) 24, 71). Larger randomised clinical trials are currently ongoing with a view to testing this hypothesis.

International patent application WO 94/29336 discloses a group of thrombin-inhibiting compounds, including HOOC—$CH_2$—(R)Cgl-Aze-Pab-H (in which Cgl represents cyclohexylglycine, Aze represents S-azetidine-2-carboxylic acid and Pab-H represents 4-aminomethylamidinobenzene), which is also known as melagatran (see Example 1 of WO 94/29336). International Patent Application WO 97/23499 discloses prodrugs of inter alia melagatran.

Eriksson et al (*Thromb. Hemost.*, (1998) 80, 1022 and *Acta Anaesthesiol. Scand.*, (2000) 44, 24) and Basu et al (*Exp. Opin. Invest. Drugs*, (2000) 9, 1129) have evaluated the effects of melagatran during experimental endotoxaemia. The latter group postulated that melagatran may be of potential use in the treatment of septic shock.

Nonetheless, neither melagatran, nor any other individual anticoagulant, has been found to be capable of providing full restitution in experimental endotoxaemia. Thus, there remains a need for alternative and/or more effective treatments of DIC.

Dexamethasone is a well-known synthetic corticosteroid that exhibits antiinflammatory activity. It may be administered in a variety of physical forms for use in the treatment of various inflammatory conditions (see, for example, *Martindale—The Complete Drug Reference*, (32$^{nd}$ Edition), K. Parfitt (ed.), Pharmaceutical Press, London (1999), at pages 1037 to 1039).

Although international patent application WO 00/41716 discloses the general use of melagatran in the treatment of inflammatory disorders, and combinations of melagatran, derivatives and prodrugs thereof with other therapeutic agents that are useful in the treatment of inflammation are mentioned in general terms, a specific combination comprising melagatran and dexamethasone is neither mentioned nor suggested.

We have now found, surprisingly, that administration of such a combination gives rise to a notable synergistic effect in experimental endotoxaemia in rats. Such a combination is thus expected to be useful in the treatment of inter alia DIC in mammalian patients.

DISCLOSURE OF THE INVENTION

According to a first aspect of the invention there is provided a combination product comprising:
(A) melagatran or a pharmaceutically-acceptable derivative thereof; and
(B) dexamethasone or a pharmaceutically-acceptable derivative thereof, wherein each of components (A) and (B) is formulated in admixture with a pharmaceutically-acceptable adjuvant, diluent or carrier.

The combination product according to the invention provides for the administration of melagatran (or derivative thereof) in conjunction with dexamethasone (or derivative thereof), and may thus be presented either as separate formulations, wherein at least one of those formulations comprises melagatran and at least one comprises dexamethasone, or may be presented (i.e. formulated) as a combined preparation (i.e. presented as a single formulation including melagatran/derivative and dexamethasone/derivative).

Thus, there is further provided:
(1) a pharmaceutical formulation including melagatran or a pharmaceutically-acceptable derivative thereof, and dexamethasone or a pharmaceutically-acceptable derivative thereof, in admixture with a pharmaceutically-acceptable adjuvant, diluent or carrier (which formulation is hereinafter referred to as a "combined preparation"); and
(2) a kit of parts comprising components:
(a) a pharmaceutical formulation including melagatran or a pharmaceutically-acceptable derivative thereof, in admixture with a pharmaceutically-acceptable adjuvant, diluent or carrier; and
(b) a pharmaceutical formulation including dexamethasone or a pharmaceutically-acceptable derivative thereof, in admixture with a pharmaceutically-acceptable adjuvant, diluent or carrier, which components (a) and (b) are each provided in a form that is suitable for administration in conjunction with the other.

According to a further aspect of the invention, there is provided a method of making a kit of parts as defined above, which method comprises bringing a component (a), as defined above, into association with a component (b), as defined above, thus rendering the two components suitable for administration in conjunction with each other.

By bringing the two components "into association with" each other, we include that components (a) and (b) of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Thus, there is further provided a kit of parts comprising:
(I) one of components (a) and (b) as defined herein; together with
(II) instructions to use that component in conjunction with the other of the two components.

The kits of parts described herein may comprise more than one formulation including an appropriate quantity/dose of melagatran or derivative thereof, and/or more than one formulation including an appropriate quantity/dose of dexamethasone or derivative thereof, in order to provide for repeat dosing. If more than one formulation (comprising either active compound) is present, such formulations may be the same, or may be different in terms of the dose of melagatran (or derivative) or dexamethasone (or derivative), chemical composition and/or physical form.

The combination products according to the invention find utility in the treatment of inflammatory disorders. Such disorders include inflammation resulting from injury, from viral or bacterial infection, or from a disease characterised by inflammation as one of its symptoms. Such diseases include autoimmune diseases, such as rheumatoid arthritis, psoriasis, allergy, asthma, rhinitis, pancreatitis, uticaria and inflammatory bowel syndrome.

The combination products according to the invention may also find utility in the treatment of patients with, or at risk of, a disease in which inhibition of thrombin is desired or required, for example:

Treatment and/or prophylaxis of thrombosis and hypercoagulability in blood and/or tissues of animals including man. It is known that hypercoagulability may lead to thromboembolic diseases. Conditions associated with hypercoagulability and thrombo-embolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thrombo-embolic disease include circulating antiphospholipid antibodies (Lupus anticoagulant), homocysteinemi, heparin induced thrombocytopenia and defects in fibrinolysis, as well as coagulation syndromes (e.g. DIC) and vascular injury in general (e.g. due to surgery).

The treatment of conditions where there is an undesirable excess of thrombin without signs of hypercoagulability, for example in neurodegenerative diseases such as Alzheimer's disease.

Disease states which may also be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation or from the left ventricle after transmural myocardial infarction, or caused by congestive heart failure; prophylaxis of re-occlusion (ie thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of DIC caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

Preferred conditions include thrombotic diseases in which inflammation plays a part in triggering coagulation. For example, inflammation in blood vessel walls due to the presence and/or the action of microbes and/or the agents released thereby, physical damage, atherscelorotic lesions and other inflammation-inducing agents.

In this regard, preferred disorders to be treated by the combination products according to the invention include DIC.

The term "DIC", which may also be referred to in the literature as diffuse intravascular coagulation, consumption coagulation and/or defibrination syndrome, will be understood to include any coagulation condition characterised as described hereinbefore, and/or in which an abnormal consumption of elements and/or factors involved in blood coagulation, fibrinolysis and/or the fibrinolytic pathway is observed as a result of their utilisation in widespread blood clotting within the vessels. DIC may result from a number of primary causes, as described hereinbefore.

Thus, a further aspect of the invention provides a method of treatment of a condition characterised by inflammation as one of its symptoms, and/or in which inhibition of thrombin is desired or required, and/or in which inflammation plays a part in triggering coagulation, which treatment comprises administration of a pharmaceutical formulation including melagatran (or a pharmaceutically-acceptable derivative thereof), and dexamethasone (or a pharmaceutically-acceptable derivative thereof, in admixture with a pharmaceutically-acceptable adjuvant, diluent or carrier.

A further aspect of the invention provides a method of treatment of such a condition, which comprises administration of:
(a) a pharmaceutical formulation including melagatran or a pharmaceutically-acceptable derivative thereof, in admixture with a pharmaceutically-acceptable adjuvant, diluent or carrier; in conjunction with
(b) a pharmaceutical formulation including dexamethasone or a pharmaceutically-acceptable derivative thereof, in admixture with a pharmaceutically-acceptable adjuvant, diluent or carrier, to a patient suffering from, or susceptible to, such a condition.

For the avoidance of doubt, as used herein, the term "treatment" includes therapeutic and/or prophylactic treatment of a condition.

With respect to the kits of parts as described herein, by "administration in conjunction with", we include that respective formulations comprising melagatran (or derivative thereof) and dexamethasone (or derivative thereof) are administered, sequentially, separately and/or simultaneously, over the course of treatment of the relevant condition, which condition may be acute or chronic.

Thus, in respect of the combination product according to the invention, the term "administration in conjunction with" includes that the two components of the combination product (melagatran/derivative and dexamethasone/derivative) are administered (optionally repeatedly), either together, or sufficiently closely in time, to enable a beneficial effect for the patient, that is greater, over the course of the treatment of the relevant condition, than if either a formulation comprising melagatran/derivative, or a formulation comprising dexamethasone/derivative, are administered (optionally repeatedly) alone, in the absence of the other component, over the same course of treatment. Determination of whether a combination provides a greater beneficial effect in respect of, and over the course of treatment of, a particular condition will depend upon the condition to be treated or prevented, but may be achieved routinely by the skilled person.

Further, in the context of a kit of parts according to the invention, the term "in conjunction with" includes that one or other of the two formulations may be administered (optionally repeatedly) prior to, after, and/or at the same time as, administration with the other component. When used in this context, the terms "administered simultaneously" and "administered at the same time as" include that individual doses of melagatran (or derivative thereof) and dexamethasone (or derivative thereof) are administered within 48 hours (e.g. 24 hours) of each other.

"Pharmaceutically-acceptable derivatives" of melagatran includes salts (e.g. pharmaceutically-acceptable non-toxic organic or inorganic acid addition salts) and solvates. It will be appreciated that the term further includes derivatives that have, or provide for, the same biological function and/or activity (e.g. inhibitory activity against thrombin) as melagatran. Moreover, for the purposes of this invention, the term also includes prodrugs of melagatran. "Prodrugs" of melagatran include any composition of matter that, following oral or parenteral administration, is metabolised in vivo to form melagatran in an experimentally-detectable amount, and within a predetermined time (e.g. within a dosing interval of between 6 and 24 hours (i.e. once to four times daily)). For the avoidance of doubt, the term "parenteral" adminstration includes all forms of adminstration other than oral administration.

Prodrugs of melagatran that may be mentioned include those disclosed in international patent application WO 97/23499. Preferred prodrugs are those of the formula $R^1O_2C$—$CH_2$—(R)Cgl-Aze-Pab-OH (see the list of abbreviations above or in WO 97/23499), wherein $R^1$ represents $C_{1-10}$ alkyl or benzyl, such as linear or branched $C_{1-6}$ alkyl (e.g. $C_{1-4}$ alkyl, especially methyl, n-propyl, i-propyl, t-butyl and, particularly, ethyl) and the OH group replaces one of the amidino hydrogens in Pab.

"Pharmaceutically-acceptable derivatives" of dexamethasone includes salts (e.g. pharmaceutically-acceptable non-toxic organic or inorganic acid addition salts) and solvates, as well as pharmaceutically-acceptable non-toxic esters. It will be appreciated that the term further includes derivatives that have, or provide for, the same biological function and/or activity as dexamethasone. Esters that may be mentioned include acetates, isonicotinates, phosphates, sodium metasulphobenzoates, sodium phosphates, hemisuccinates, linoleates, palmitates, pivalates, propionates, sodium succinates, tebutates, valerates, phenpropionates and troxundates of dexamethasone.

In accordance with the invention, melagatran, dexamethasone and derivatives of either, may be administered orally, intravenously, subcutaneously, buccally, rectally, dermally, nasally, tracheally, bronchially, topically, by any other parenteral route, or via inhalation, in the form of a pharmaceutical preparation comprising melagatran and/or dexamethasone in a pharmaceutically-acceptable dosage form. Depending on the disorder, and the patient, to be treated, as well as the route of administration, the compositions may be administered at varying doses.

Preferred modes of delivery are systemic. For melagatran and derivatives thereof, preferred modes of administration are parenteral, more preferably intravenous, and especially subcutaneous. For prodrugs of melagatran, preferred modes of administration are oral. For dexamethasone and derivatives thereof, preferred modes of administration are oral, parenteral (e.g. intravenous injection or infusion, intramuscular, intraarticular or intralesional injection, or soft-tissue injection), or, if appropriate, topical, for example by inhalation to the lung or nasally.

In the therapeutic treatment of mammals, and especially humans, melagatran/derivatives and dexamethasone/derivatives will be administered as pharmaceutical formulations in admixture with pharmaceutically-acceptable adjuvants, diluents or carriers, which may be selected with due regard to the intended route of administration and standard pharmaceutical practice.

Suitable formulations for use in administering melagatran and derivatives (including prodrugs) thereof are described in the literature, for example as described in inter alia international patent applications WO 94/29336, WO 96/14084, WO 96/16671, WO 97/23499, WO 97/39770, WO 97/45138, WO 98/16252, WO 99/27912, WO 99/27913, WO 00/12043 and WO 00/13671, the disclosures in which documents are hereby incorporated by reference.

Similarly, suitable formulations for use in administering dexamethasone are described in the literature (see for example Martindale—*The Complete Drug Reference* (32$^{nd}$ Edition) at pages 1037 to 1039 and the documents referred to therein, the relevant disclosures in all of which documents are hereby incorporated by reference). Otherwise, the preparation of suitable formulations, and in particular combined preparations including both melagatran/derivative and dexamethasone/derivative may be achieved non-inventively by the skilled person using routine techniques.

The amounts of melagatran/derivative and dexamethasone/derivative in the respective formulation(s) will depend on the severity of the condition, and on the patient, to be treated, as well as the compound(s) which is/are employed, but may be determined non-inventively by the skilled person.

Suitable doses of melagatran/derivatives and dexamethasone/derivatives in the therapeutic and/or prophylactic treatment of mammalian, especially human, patients may be determined routinely by the medical practitioner or other skilled person, and include the respective doses discussed in the prior art documents relating to both that are mentioned hereinbefore, the relevant disclosures in which documents are hereby incorporated by reference.

In the case of melagatran, suitable doses of active compound, prodrugs and derivatives thereof in the therapeutic and/or prophylactic treatment of mammalian, especially human, patients include those which give a mean plasma concentration of up to 5 µmol/L, for example in the range 0.001 to 5 µmol/L over the course of treatment of the relevant condition. Suitable doses may thus be in the range 0.1 mg once daily to 25 mg three times daily, and/or up to 100 mg infused parenterally over a 24 hour period, for melagatran, and in the range 0.1 mg once daily to 100 mg three times daily for prodrugs of melagatran including those specifically mentioned hereinbefore.

In the case of dexamethasone and derivatives thereof, suitable doses for therapeutic or prophylactic purposes are in the range 0.001 to 1 mg/kg body weight daily.

In any event, the physician, or the skilled person, will be able to determine the actual dosage which will be most suitable for an individual patient, which is likely to vary with the condition that is to be treated, as well as the age, weight, sex and response of the particular patient to be treated. The above-mentioned dosages are exemplary of the average case; there can, of course, be individual instances where higher or lower dosage ranges are merited, and such are within the scope of this invention.

When separate formulations are administered, the sequence in which the formulations comprising melagatran (or derivative thereof), and dexamethasone (or derivative thereof), may be administered (i.e. whether, and at what point, sequential, separate and/or simultaneous administration takes place) may be determined by the physician or skilled person. For example, the sequence may depend upon many factors that will be evident to the skilled person, such as whether, at any time during the course or period of treatment, one or other of the formulations cannot be administered to the patient for practical reasons (e.g. the patient is unconscious and thus unable to take an oral formulation comprising either melagatran or dexamethasone).

The method described herein may have the advantage that, in the treatment of conditions such as DIC, it may be more convenient for the physician and/or patient than, be more efficacious than, be less toxic than, have a broader range of activity than, be more potent than, produce fewer side effects than, or that it may have other useful pharmacological properties over, similar methods known in the prior art for the treatment of such conditions.

The invention is illustrated, but in no way limited, by the following examples with reference to the figures in which:

FIG. 3b illustrates fibrin accumulation in the spleen 5 h after adminstration of endotoxin for various groups of rats. (control groups and those administered test compounds).

EXAMPLE

Materials and Methods

Figure 1:
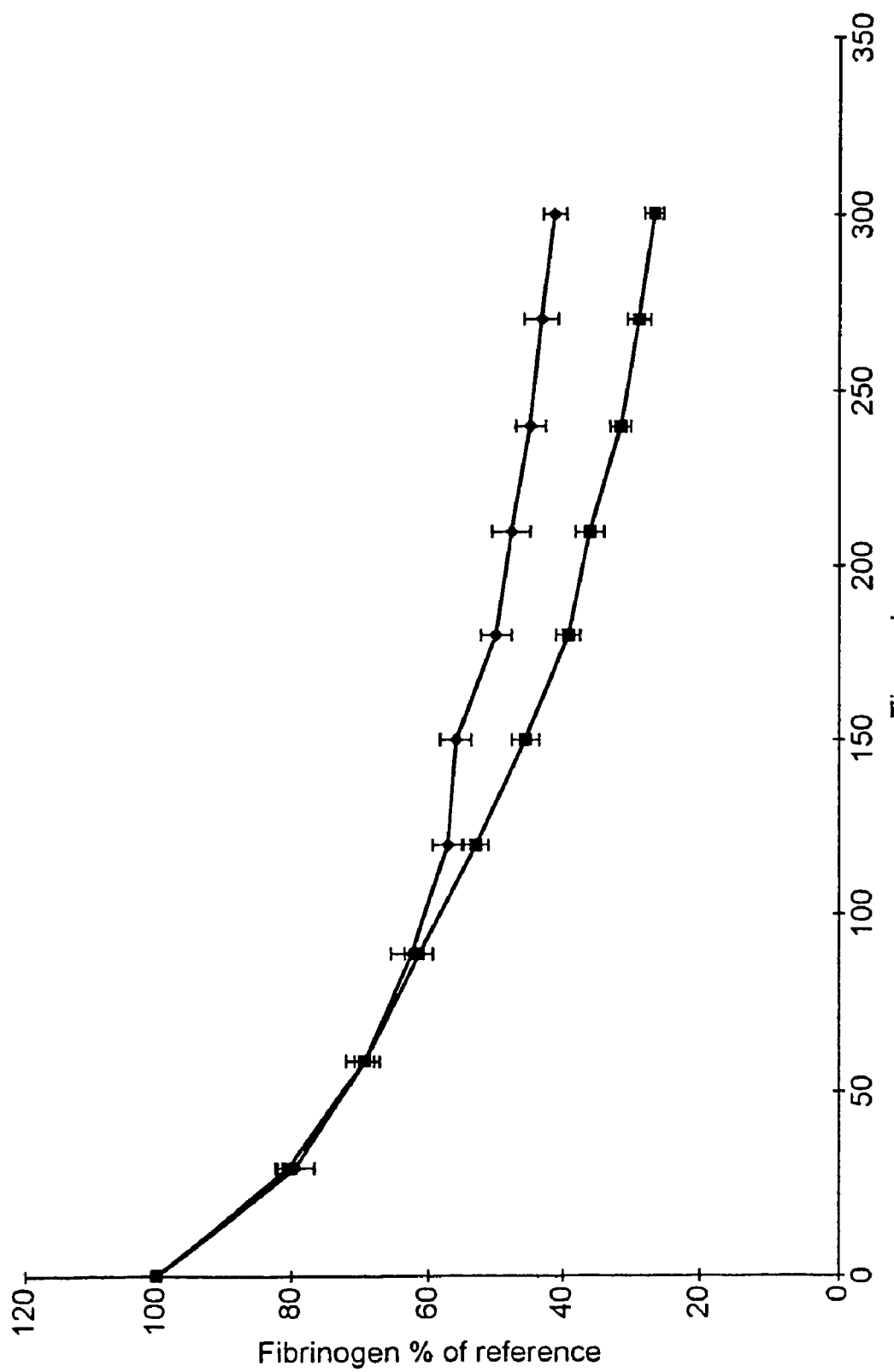
FIG. 1 illustrates the decrease in plasma fibrinogen in control groups (sham group: diamonds; vehicle group: squares) of rats over a 5 hour period after the iv injection of endotoxin.

Male Sprague-Dawley rats (body weight 350-425 g, Möllegaard Breeding Centre, Skensved, Denmark) were used in the study. Animal care and use was approved by Gothenburg Local Ethical Committee on Animal Experiments, a body within The National Board for Laboratory Animals, Sweden. Anaesthesia was induced with an intraperitoneal injection of sodium pentobarbital (80 mg/kg, NordVacc, Malmo, Sweden) and followed by a continuous infusion (12 mg/kg/h) throughout the experiment. The body temperature was maintained at. 38° C. throughout the experiment by external heating.

Endotoxin (lipopolysaccaride, LPS, *Escherichia coli*, 055: B5, Sigma, Ma, USA) was given as a bolus iv injection at the start of the experiment. The fibrinolytic inhibitor, tranexamic acid (Cyclokapron®, Kabi Pharmacia, Stockholm, Sweden) was given (as a comparison) as one iv injection just before the endotoxin and one more injection 2.5 h later. Unfractionated sodium heparin (heparin) from intestinal mucous (Kabi Pharmacia) and melagatran (AstraZeneca, Södertälje, Sweden) were given as bolus iv injections and were followed by continuous infusion throughout the experiment starting twenty minutes before an injection of endotoxin. Dexamethasone (Decadron®), MSD, Haarlem, Netherlands) was given as a bolus iv injection 1 h before the endotoxin. Sham operated animals received saline instead of endotoxin. For details of doses and group number see Table 1.

TABLE 1

| Group | Abbrev. | Size | Drug | Bolus | Infusion |
|---|---|---|---|---|---|
| I | Sham | 13 | Saline | | |
| II | Vehicle | 16 | Saline | | |
| III | tranexamic acid | 7 | tranexamic acid | 2 × 50 mg/kg | |
| IV | Mela low | 10 | Melagatran | 0.13 μmol/kg | 0.32 μmol/kg/h |
| V | Mela med | 10 | Melagatran | 0.4 μmol/kg | 1.0 μmol/kg/h |
| VI | Mela high | 9 | Melagatran | 1.3 μmol/kg | 3.2 μmol/kg/h |
| VII | Hep low | 8 | Heparin | 25 U/kg | 25 U/kg/h |
| VIII | Hep med | 5 | Heparin | 50 U/kg | 50 U/kg/h |
| IX | Hep low | 8 | Heparin | 25 U/kg | 25 U/kg/h |
| | Mela low | | Melagatran | 0.13 μmol/kg | 0.32 μmol/kg/h |
| X | Hep low | 7 | Heparin | 25 U/kg | 25 U/kg/h |
| | Mela med | | Melagatran | 0.4 μmol/kg | 1.0 μmol/kg/h |
| XV | Dexa low | 5 | Dexamethasone | 1 mg/kg | |
| XVI | Dexa high | 5 | Dexamethasone | 10 mg/kg | |
| XVII | Dexa low | 5 | Dexamethasone | 1 mg/kg | |
| | Mela low | | Melagatran | 0.13 μmol/kg | 0.32 μmol/kg/h |
| XVIII | Dexa low | 5 | Dexamethasone | 1 mg/kg | |
| | Mela high | | Melagatran | 0.4 μmo//kg | 1.0 μmol/kg/h |
| XIX | Dexa high | 6 | Dexamethasone | 10 mg/kg | |
| | Mela low | | Melagatran | 0.13 μmol/kg | 0.32 μmol/kg/h |
| XX | Dexa high | 4 | Dexamethasone | 10 mg/kg | |
| | Mela low | | Melagatran | 0.4 μmol/kg | 1.0 μmol/kg/h |

The animals were tracheotomized, and catheters were placed in the left jugular vein for drug administrations and in the right femoral artery for continuous infusion of pentobarbital and blood sampling. Endotoxin (1 mg/kg) was given as an intravenous injection at the start of the experiment. Human $^{125}$I-fibrinogen (80 kBq, IM53, Amersham International, Buckinghamshire, UK) was given intravenously 15 minutes before endotoxin as a marker of fibrinogen in the blood and fibrin in the organs. Blood samples were taken every 30 minutes for measurement of $^{125}$I-activity in the blood, determination of blood cells and haemoglobin (Hb) content. At 2.5 and 5 hours after the administration of endotoxin, blood samples were taken for determination of plasmin activator inhibitor (PAI-1) activity in the plasma, and of plasma concentration of melagatran and heparin. In some animals, the amount of thrombin/antithrombinIII complex (TAT) formed was also measured. Five hours after endotoxin injection, the lungs, liver, kidneys and the spleen were removed from the animals, externally rinsed with saline and blotted dry, and $^{125}$I-activity measured.

Blood samples were drawn into plastic tubes containing citrate solution (9 parts of blood and 1 part of sodium citrate solution, 0.13 mol/L), centrifuged at 10 000×g for 5 min at 20° C., and the plasma was stored at −20° C. prior to analysis. APTT (activated prothrombin time, PTT-Automate (Diagnostica Stago, Asniéres, France) was determined according to the manufacturer's instruction in a coagulometer (KC4, Amelung, Lemago, Germany). Plasma concentration of melagatran was determined with a LC-MS method (BA-285, AstraZeneca R&D Mölndal, Sweden) and the plasma concentration of heparin was determined by Coatest Heparin (Cromogenix, Mölndal, Sweden). Thrombin/antithrombin III complex (TAT) was determined with TAT-micro (Stago, Arnisiére, France). PAI-1 activity was measured with Spectrolyse/Fibrin (Biopool, Umeå, Sweden). Blood cells and haemoglobin (Hb) were determined with a cellcounter (Sysmex F-800, TOA Medical Electronics Co, Kobe, Japan) and the measurements obtained just before the endotoxin-injection (baseline values) were set to 100%.

$^{125}$I-activity in the blood samples and the organs (lungs, kidneys, liver and spleen) were measured in a gamma counter (1282 Compugamma, LKB Wallac Oy, Turku, Finland) on the same day as the experiment was performed and calculated as the activity/mg of the blood or the organ. The fibrinogen in the blood and the fibrin incorporated in the organs were calculated as the percentage of the $^{125}$I-activity in the blood or the organs (cpm/mg) and the activity of the reference blood sample (baseline value) taken just before the endotoxin-injection at the start of the experiment.

Results are expressed as mean values and standard error of the means (SEM). The repeated measurements of fibrinogen and platelet counts in the blood during the experiment were analysed using a two-way anova with factors group and time and the interaction group*time. Adjustment for multiplicity was done using Scheffe. Fibrinogen and fibrin in the organs and platelet counts at 150 minutes experimental time were analysed using one-way anova and in case of p<0.05 followed by pair-wise comparisons against the sham operated group (no endotoxin), and the vehicle group only given endotoxin. Corrections for multiple comparisons were made according to Bonferroni.

Results

Fibrinogen and Fibrin $^{125}$I-activity in the blood samples was used as a measurement of the amount of fibrinogen in the blood.

FIG. 1 shows that the plasma fibrinogen in the sham and vehicle groups decreased over a 5 hour period after the iv injection. After 150 minutes, and throughout the experiment, there was a significant decrease in fibrinogen in the blood of rats given endotoxin compared to the sham operated rats.

Figure 2:
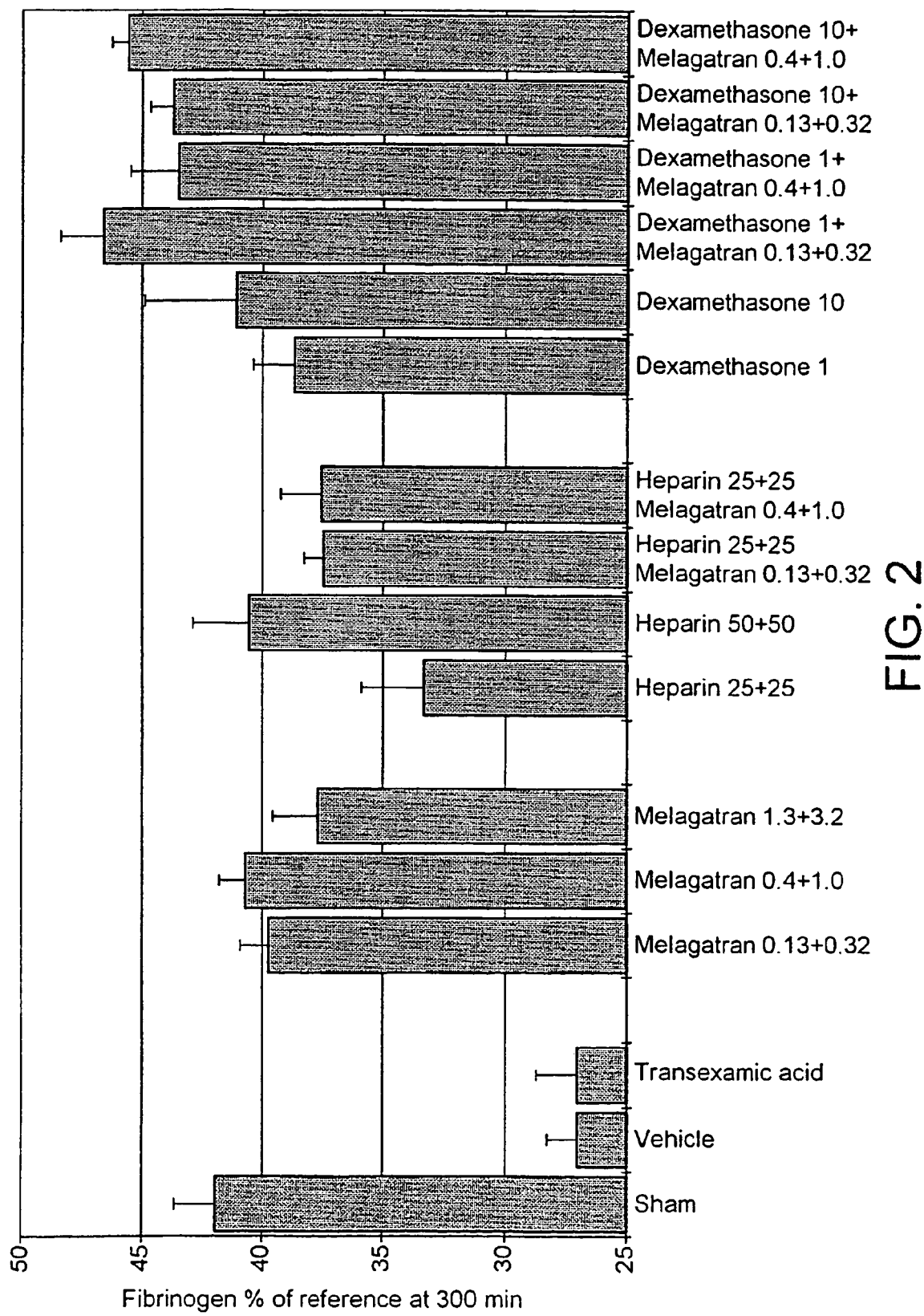
FIG. 2 illustrates the fibrinogen in blood 5 h after adinstration of endotoxin for various groups of rats (control groups and those administered test compounds).

FIG. 2 shows the fibrinogen in blood 5 h after endotoxin. In the vehicle group II (27±1.3%), group III (tranexamic acid) and group VII (Hep low), fibrinogen was significantly decreased compared to the sham operated group I (42±1.7%).

Figure 3A:
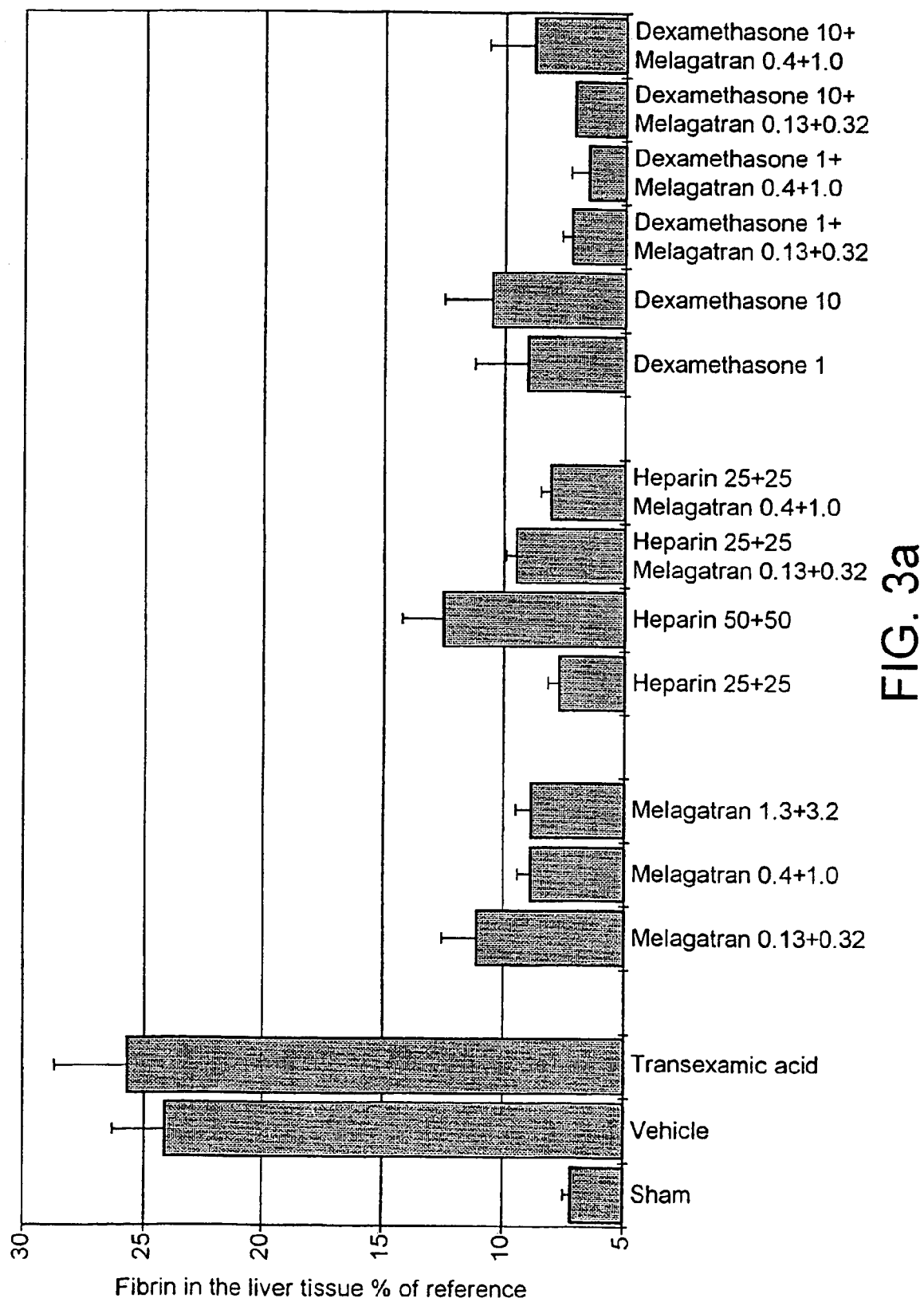
FIG. 3a illustrates fibrin accumulation in the liver 5 h after adminstration of endotoxin for various groups of rats (control groups and those administered test compounds).

In the liver (FIG. 3a) and the spleen (FIG. 3b), a significant increase in fibrin accumulation was found in group II (Veh) and group III (tranexamic acid) when compared to the sham operated rats (group I). In the lung and the kidneys no such accumulation of fibrin was found.

Platelets in the Blood

Figure 4:
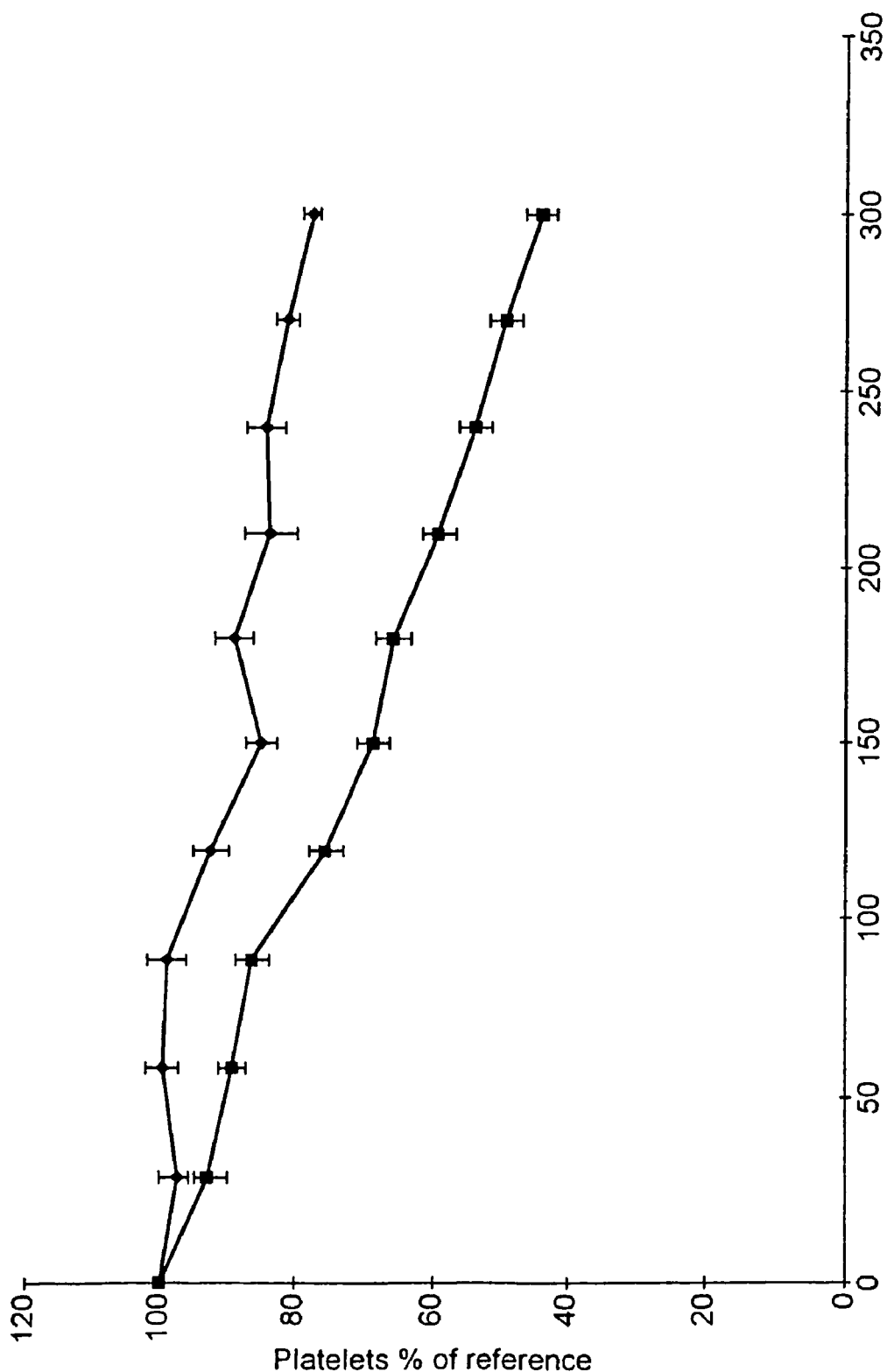
FIG. 4 illustrates the decrease in platelets in control groups (sham group: diamonds; vehicle group: squares) of rats over a 5 hour period after the iv injection of endotoxin.
Figure 5:
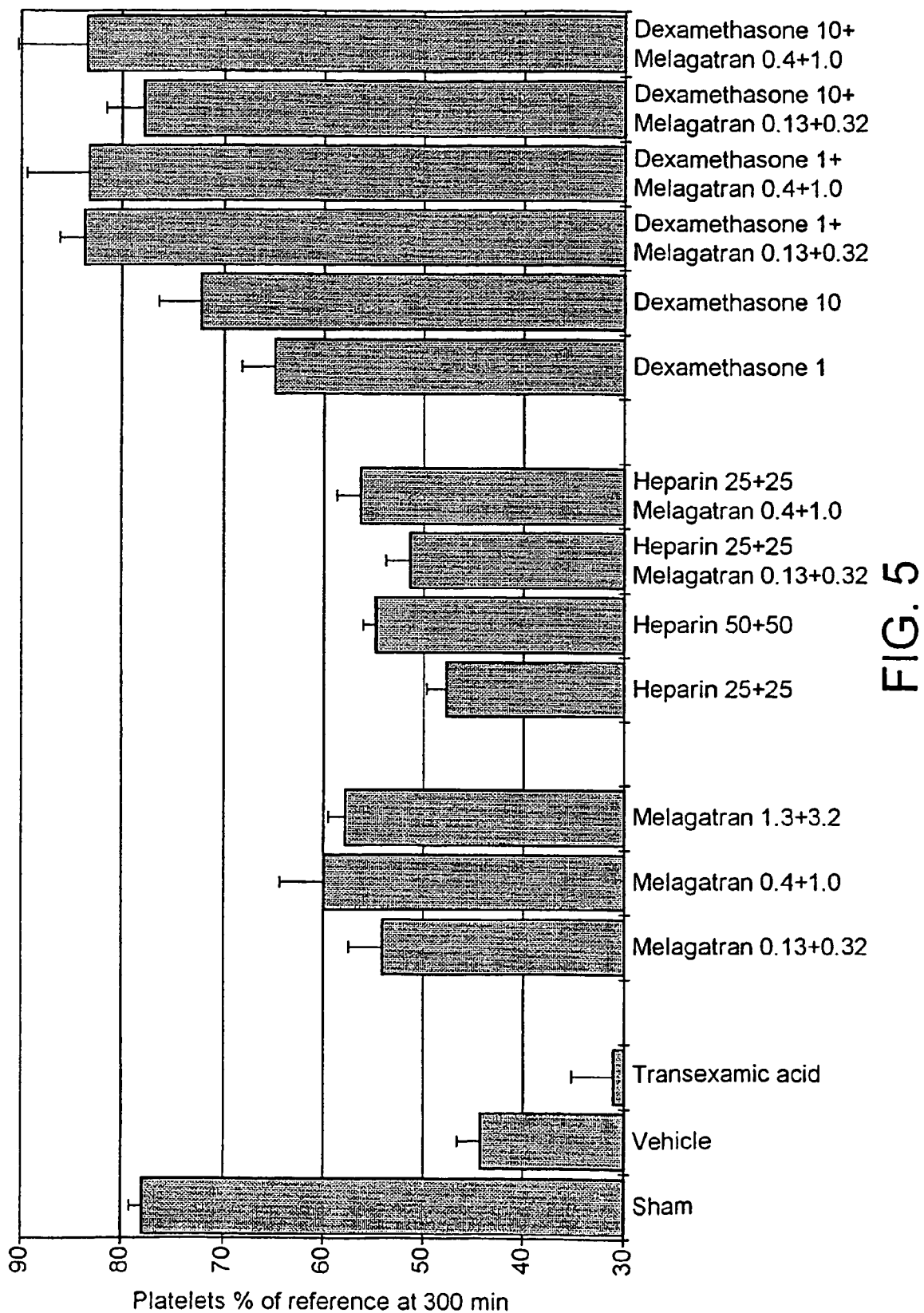
FIG. 5 illustrates the platelets in percent of the basal value 5 h after adminstration of endotoxin for various groups of rats (control groups and those administered test compounds).

As for fibrinogen, there was a decrease of platelets during the 5 h experiment (sham and vehicle groups, FIG. 4) although less pronounced. The platelets decreased in the sham group 1 to 78±2.2% and in the vehicle group II given endotoxin to 43±2.6%. FIG. 5 shows the platelets in percent of the basal value at 5 h for all the groups. Five hours after administration, endotoxin platelets were significantly decreased compared to the sham operated group I in all the groups except in groups XV-XX (dexamethasone low and dexamethasone high with or without addition to melagatran low and melagatran med).

TAT

TAT was measured in some animals. In group I (sham) TAT was 4.7±2.5 µg/l and increased in group II (Veh) to 39.7±3.3 µg/l and in the group III (TA) to 55.5±6.6 µg/l, respectively. In groups XV-XX (dexamethasone with or without melagatran) TAT was ≦10 µg/l indicating attenuated thrombin generation.

PAI-1

The PAI-1 activity in the sham-operated rats (group I) was 81±15 U/ml at 5 h experimental time. Three animals had values below limit of detection (50 U/ml). These values were handled as 50 U/ml. In all the groups given endotoxin, the PAI-1 activity was increased to more than 350 U/ml 2.5 h after the LPS injection and remained at this level at 5 h. None of the treatments used in this study affected the plasma levels of PAI-1.

Plasma Concentration

The mean plasma concentrations during the 5 h experiment for the three melagatran groups (IV, V and VI) were 0.78±0.08, 2.83+0.45 and 6.88±0.42 µmol/l, respectively. When combined with heparin, the plasma concentrations for melagatran (groups IX and X) were 0.72±0.09, 1.97±0.16 µmol/l. When melagatran was given in combination with dexamethasone (groups XVII-XX) the plasma concentrations were 0.48±0.01 and 0.46±0.02 µmol/l for the low dose groups and 1.49±0.13, and 1.28±0.1 µmol/l for the high dose groups. For the heparin groups the plasma concentrations were 0.37±0.03, 0.26±0.08 and 0.32±0.02 U/ml for the low groups (VII, IX and X) and 1.01±0.08 U/ml for the high dose heparin (group VIII), respectively.

Discussion

In this study PAI-1 was used as an activation marker of hemostasis after the administration of endotoxin. The high PAI-1-activity 2.5 h after endotoxin administration and throughout the experiment indicates a sustained activation state. No treatment options used in this study had any overt impact on the PAI-1 activity in plasma.

Platelets

Platelet consumption was only partially reduced by all three agents (the two anticoagulants and dexamethasone) when used in isolation in the doses employed in this study. By way of contrast, the combination of melagatran and dexamethasone completely prevented platelet consumption (84±2.6% and 83±6.3% for group XVII and XVIII (Dexa low+Mela low and Dexa low+Mela med) and 78±3.7% and 83±6.8% for groups XIX and XX (Dexa high+Mela low and Dexa high+Mela med)), respectively.

Fibrinogen and Fibrin

Human $^{125}$I-labelled fibrinogen is often used as a tracer for fibrinogen in the blood and fibrin in the organs. Over the initial 90 min of the experiment 38% of the $^{125}$I-activity was lost to the same extent in group I (sham) as in group II (vehicle). This rapid loss of activity from the blood was probably due to elimination of free iodide as well as of small labelled fragments of fibrinogen or fibrin by the kidneys. Ninety min after endotoxin administration, the fibrinogen curves deviated with a further decline of 20% in the sham group (I) and 32% in the vehicle group (II) over the next 210 min. For the low dose heparin (group VII), the fibrinogen consumption was as high as for the vehicle group (I). High dose heparin (group VIII) and melagatran without (groups IV-VI) or with dexamethasone (groups XVII-XX) completely prevented fibrinogen consumption.

TAT

TAT increased during the experiment indicating increased thrombin generation in the groups given endotoxin. In the dexamethasone groups the thrombin generation was suppressed to below 8 µg/l.

In summary, these experiments indicate that, of the agents employed, only a combination of melagatran and dexamethasone completely protected subject animals from the development of DIC.

The invention claimed is:

1. A combination product comprising:
    (A) melagatran or a pharmaceutically-acceptable salt, solvate or prodrug thereof; and
    (B) dexamethasone or a pharmaceutically-acceptable salt, solvate or ester thereof, wherein each of components (A) and (B) is formulated in admixture with a pharmaceutically-acceptable adjuvant, diluent or carrier.

2. A combination product as claimed in claim 1 which comprises a pharmaceutical formulation comprising
    melagatran or a pharmaceutically-acceptable salt, solvate or prodrug thereof,
    dexamethasone or a pharmaceutically-acceptable salt, solvate or prodrug thereof, and
    a pharmaceutically-acceptable adjuvant, diluent or carrier.

3. A method of treating a condition characterized by inflammation as one of its symptoms, and/or in which inhibition of thrombin is desired or required, and/or in which inflammation plays a part in triggering coagulation, comprising administering an effective amount of the pharmaceutical formulation as claimed in claim 2 to reduce the inflammation to a patient suffering from, or susceptible to, such a condition.

4. A combination product as claimed in claim 1 which comprises a kit of parts comprising:
    (a) a pharmaceutical formulation comprising melagatran or a pharmaceutically-acceptable salt, solvate or prodrug thereof in admixture with a pharmaceutically-acceptable adjuvant, diluent or carrier; and
    (b) a pharmaceutical formulation comprising dexamethasone or a pharmaceutically-acceptable salt, solvate or ester thereof, in admixture with a pharmaceutically-acceptable adjuvant, diluent or carrier,
    wherein (a) and (b) are each provided in a form that is suitable for administration in conjunction with the other.

5. A kit of parts as claimed in claim 4, wherein the pharmaceutical formulations (a) and (b) are suitable for sequential, separate and/or simultaneous use in the treatment of a condition characterized by inflammation as one of its symptoms, and/or in which inhibition of thrombin is desired or required, and/or in which inflammation plays a part in triggering coagulation.

6. The kit of parts as claimed in claim 5, wherein the condition is disseminated intravascular coagulation.

7. A kit of parts comprising:
    (I) one of the pharmaceutical formulations (a) and (b) as claimed in claim 4; and (II) instructions how to use that pharmaceutical formulation in conjunction with the other of the two pharmaceutical formulations.

8. A method of making a kit of parts as claimed in claim 4 comprising
bringing the pharmaceutical formulation of (a) into association with the pharmaceutical formulation of (b), thus rendering the pharmaceutical formulations (a) and (b) suitable for administration in conjunction with each other.

9. A method of treating a condition characterized by inflammation as one of its symptoms, and/or in which inhibition of thrombin is desired or required, and/or in which inflammation plays a part in triggering coagulation, comprising administering the kit of parts as claimed in claim 4 in an amount effective to reduce the inflammation to a patient suffering from, or susceptible to, such a condition.

10. The combination product as claimed in any one of claims 1 to 4, wherein the prodrug of melagatran is of the formula $R^1O_2C-CH_2-(R)Cgl$-Aze-Pab-OH, wherein $R^1$ represents linear or branched $C_{1-6}$ alkyl and the OH group replaces one of the amidino hydrogens in Pab.

11. The combination product as claimed in claim 10, wherein $R^1$ represents methyl, ethyl, n-propyl, i-propyl or t-butyl.

12. The combination product as claimed in claim 11, wherein $R^1$ represents ethyl.

13. A method of treating a condition characterized by inflammation as one of its symptoms, and/or in which inhibition of thrombin is desired or required, and/or in which inflammation plays a part in triggering coagulation, comprising administering an effective amount of the combination product as claimed in claim 1 to reduce the inflammation to a patient suffering from, or susceptible to, such a condition.

14. The method as claimed in claim 13, wherein the condition is disseminated intravascular coagulation.

* * * * *